United States Patent [19]

Jaeger

[11] Patent Number: 4,615,334
[45] Date of Patent: Oct. 7, 1986

[54] SURGICAL PAD FOR GYNECOLOGICAL PROCEDURES

[76] Inventor: John C. Jaeger, 3584 Batavia-Elba TLR, Oakfield, N.Y. 14125

[21] Appl. No.: 755,345

[22] Filed: Jul. 16, 1985

[51] Int. Cl.⁴ .............................................. A61B 1/32
[52] U.S. Cl. .................................................... 128/17
[58] Field of Search ............. 128/3, 17, 18, 20, 303 R, 128/321, 323; 604/385

[56] References Cited

U.S. PATENT DOCUMENTS

| | | | |
|---|---|---|---|
| 3,841,317 | 10/1974 | Awais | 128/17 |
| 3,851,642 | 12/1974 | McDonald | 128/18 |
| 4,492,220 | 1/1985 | Hayes | 128/17 |

Primary Examiner—John D. Yasko
Attorney, Agent, or Firm—Lalos, Keegan & Kaye

[57] ABSTRACT

A surgical pad adapted for use with a speculum blade insertable into the vaginal cavity of a patient, in performing a dilation a curettage procedure, generally comprising a pad disposable on the speculum blade for collecting curetted tissue, the pad having straps or an adhesive section on the underside thereof for securing the pad on the speculum blade to facilitate insertion of the pad on the speculum blade into the vaginal cavity and to prevent displacement of the pad relative to the speculum blade when performing curettage of the uterine canal. The periphery of the upper side of the pad is provided with an adhesive surface area covered by a removable strip which may be removed after curetted tissue has been collected on the pad to permit the pad to be folded onto itself and adhesively secured together to enclose the curetted tissue.

13 Claims, 10 Drawing Figures

SURGICAL PAD FOR GYNECOLOGICAL PROCEDURES

This application is a continuation-in-part application of Ser. No. 640,600, filed Aug. 14, 1984.

This invention relates to a surgical pad and more particularly to a surgical pad adapted for use with a speculum blade in performing a dilation and curettage procedure.

In performing a typical dilation and curettage procedure, the patient is initially anaesthetized and placed in a dorsal lithotomy position. A weighted speculum is then inserted in the vaginal cavity of the patient with the blade portion thereof resting on the bottom wall of the cavity. The depth of the uterine cavity is then determined by a sounding technique and the cervical canal is then dilated in a conventional manner. With the cervical canal dilated and the speculum blade in place, a gauze pad is placed on the speculum blade and the uterus is surgically scraped. The curetted tissue consisting of strips and flakes is scraped rearwardly and collected on the gauze pad to be removed from the vaginal cavity for further examination by a pathologist.

In performing such a procedure, it has been found that in the process of curetting the uterus, the pad placed on the speculum blade for collecting the curetted tissue becomes easily displaced, resulting in a loss of curetted tissue in the vagina which must be retrieved by wiping out the upper region of the vagina. It also has been found to be difficult to recover curetted tissue from meshed gauze in that the smaller strips and flakes of the curetted tissue tend to adhere to the meshed gauzed material. From a pathologist's point of view, it would be more desirable to have the curetted tissue specimen delivered on a pad having a solid or smooth surface so that all of the specimen may be recovered for examination purposes. The use of a pad with an imperforate or smooth surface, however, simply would render the pad more apt to displace when positioned on the speculum blade during the curettage operation, thus further adversely affecting the collection of the curetted tissue. It thus has been found to be desirable to provide an improved pad for use in dilation and curettage procedures which would obviate the aforementioned problems attendant to surgical pads presently in use for such purposes.

Accordingly, it is the principal object of the present invention to provide an improved surgical pad.

Another object of the present invention is to provide an improved surgical pad for use in gynecological procedures.

A further object of the present invention is to provide an improved surgical pad adapted for use in dilation and curettage procedures.

A still further object of the present invention is to provide an improved surgical pad positionable on a speculum blade for collecting curetted tissue in dilation and curettage procedures.

Another object of the present invention is to provide an improved surgical pad positionable on a speculum blade for use in dilation and curettage procedures which is prevented from becoming displaced relative to the speculum blade when the uterus is being curetted.

A further object of the present invention is to provide an improved surgical pad usable with a speculum blade in dilation and curettage procedures which may be easily inserted and removed from the vaginal cavity, positioned on a speculum blade.

A still further object of the present invention is to provide an improved surgical pad adapted for use in dilation and curettage procedures for collecting curetted tissue.

Another object of the present invention is to provide an improved surgical pad adapted for use in dilation and curettage procedures for collecting curetted tissue which permits the curetted tissue to be preserved on the pad and readily recovered for examination purposes.

A further object of the present invention is to provide an improved surgical pad adapted for use in gynecological procedures which is relatively simple in construction, relatively inexpensive to manufacture and easy to use.

Other objects and advantages of the present invention will become more apparent to those having ordinary skill in the art to which the present invention pertains from the following description taken in conjunction with the accompanying drawings, wherein.

Figure 3:
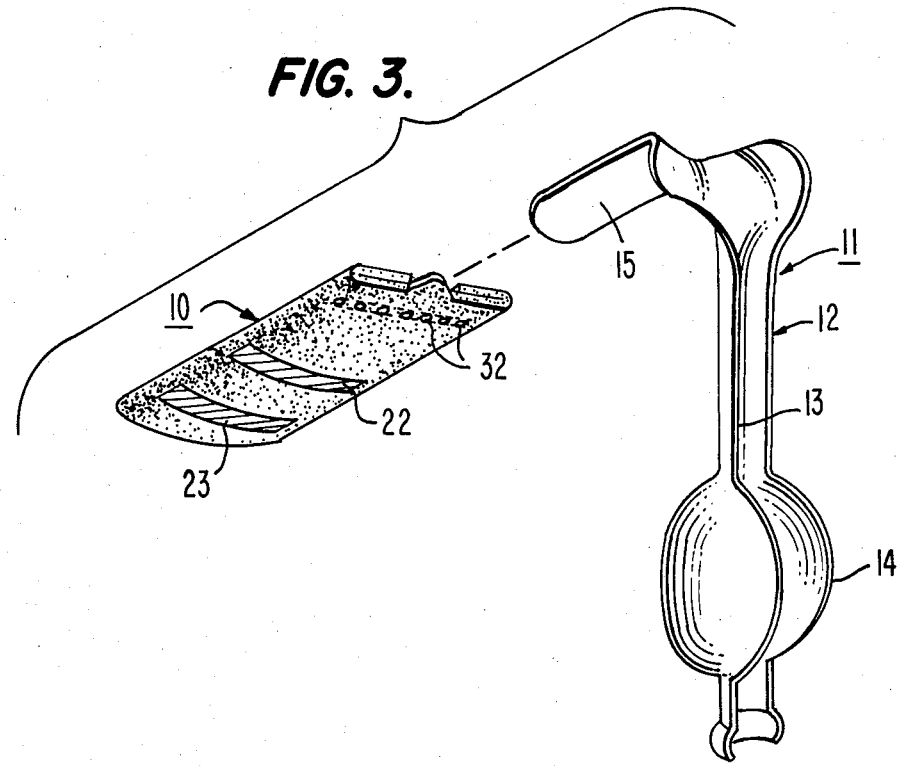
FIG. 3 is a perspective view of the pad shown in FIGS. 1 and 2, illustrated in a condition to be positioned on a speculum blade.

Referring to the drawings, there is illustrated a surgical pad 10 which is adapted for use with a vaginal speculum 11. As best shown in FIG. 3, the speculum generally includes an elongated handle section 12 provided with a recessed portion 13 to facilitate drainage and lower enlarged portion 14 for weighting the speculum, and a blade section 15 formed integral with the upper end of the handle section and disposed substantially perpendicular thereto. In the conventional manner, a surgical pad is adapted to be positioned on the upper surface of the speculum blade to be inserted with the speculum blade into the vaginal cavity of a patient.

The surgical pad 10 has a substantially rectangular configuration and includes an upper side 16, an underside 17, front and rear edges 18 and 19, and side edges 20 and 21. Rear edge 19 is provided with a tab 19a to facilitate grasping and manipulating the pad.

Figure 1:
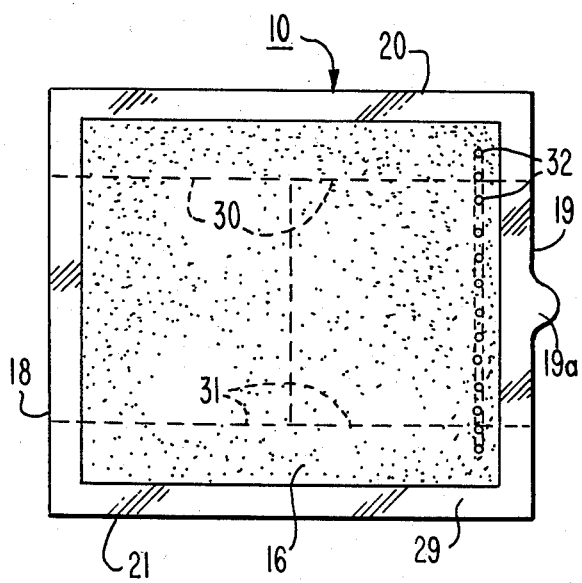
FIG. 1 is a top plan view of a surgical pad embodying the present invention.
Figure 2:
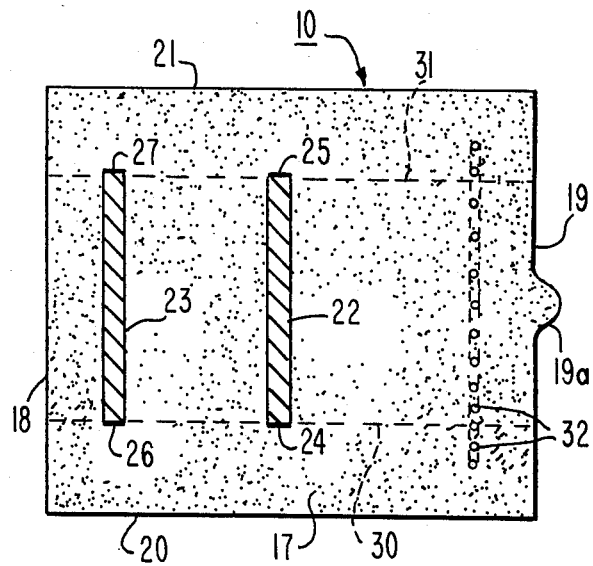
FIG. 2 is a bottom plan view of such pad showing one embodiment of the pad adapted to be secured on a speculum blade in accordance with the present invention.

As shown in FIGS. 2 and 3, the underside of the pad has attached thereto two straps 22 and 23. Strap 22 is attached to the pad at end points 24 and 25 and strap 23 is attached to the pad at end points 26 and 27. The straps maybe formed of any clinically suitable material including paper, plastic, and fabric. The straps can be attached to the pad in any conventional manner including sewing, application of adhesive material, or mechanical fixtures. The straps are attached to the underside of the pad to receive and secure the speculum blade 15. The pad is positioned on the speculum blade by sliding the pad on the blade with the leading end of the blade first passing between strap 22 and the underside of the pad and then passing between the strap 23 and the underside of the pad. The pad is then prevented from displacing relative to the speculum blade by virtue of the forward end of the blade being held in place by strap 23 and the back of the blade being held in place by strap 22. In addition, it is contemplated that the two straps could be replaced by a single strap or any number of straps attached to the underside of the pad to secure the pad to the speculum blade.

Figure 4:
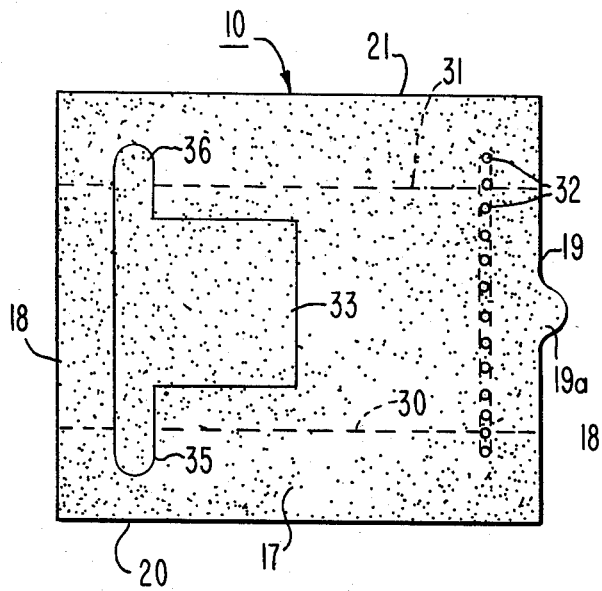
FIG. 4 is a bottom plan view of such pad showing a backing piece covering a securing section of the pad in a second embodiment of the pad adapted to be secured on a speculum blade.
Figure 5:
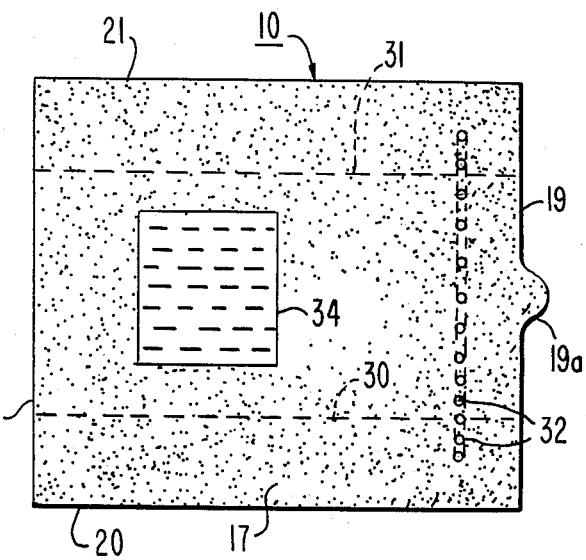
FIG. 5 is a bottom plan view of the pad showing a second embodiment of the pad adapted to be secured on a speculum blade.
Figure 6:
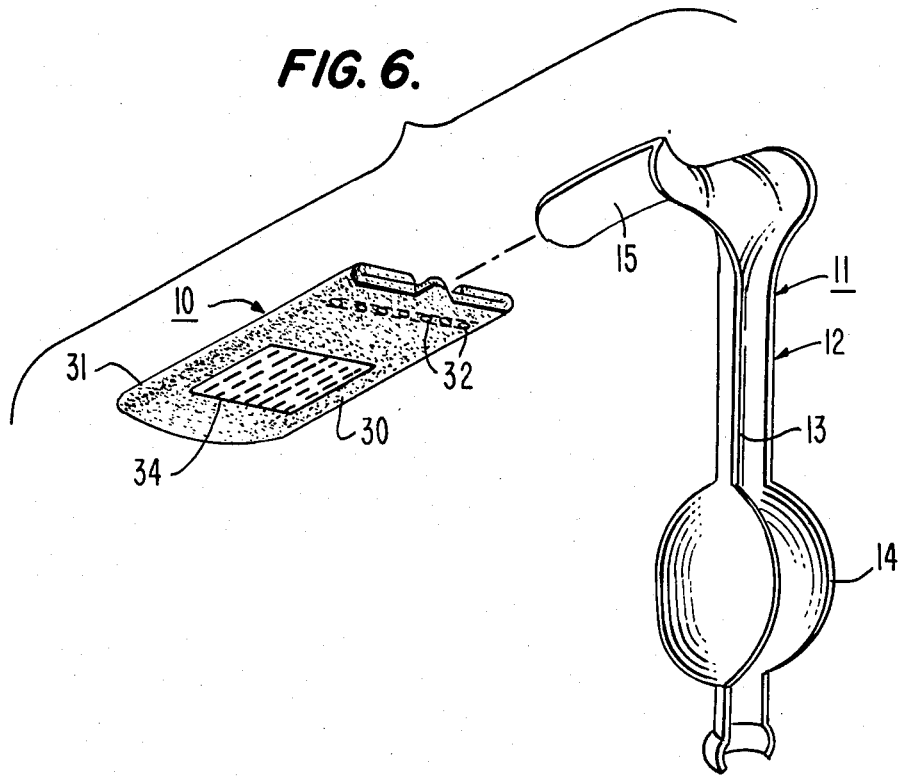
FIG. 6 is a perspective view of the pad shown in FIGS. 1 and 5, illustrated in a condition to be positioned on a speculum blade.

An alternate method of securing the pad to the speculum blade is shown in FIGS. 4, 5, and 6. On the underside of the pad is a backing piece 33 (FIG. 4) covering an adhesive section 34 of the pad (FIG. 5). Backing piece 33 has two tabs 35 and 36 extending beyond the lateral margins 30 and 31 of a folded pad for easy removal of the backing. Backing 33 is pulled off from the pad by gripping tabs 35 and/or 36 and pulling back. Exposed beneath backing 33 is adhesive section 34 of the pad having dimensions generally corresponding to the dimensions of the upper surface of speculum blade 15. The pad is positioned on the speculum blade by placing adhesive section 34 of the pad onto the upper surface of the blade. Movement of the pad relative to the blade is prevented by the adhesive bond formed between the pad and blade.

Figure 7:
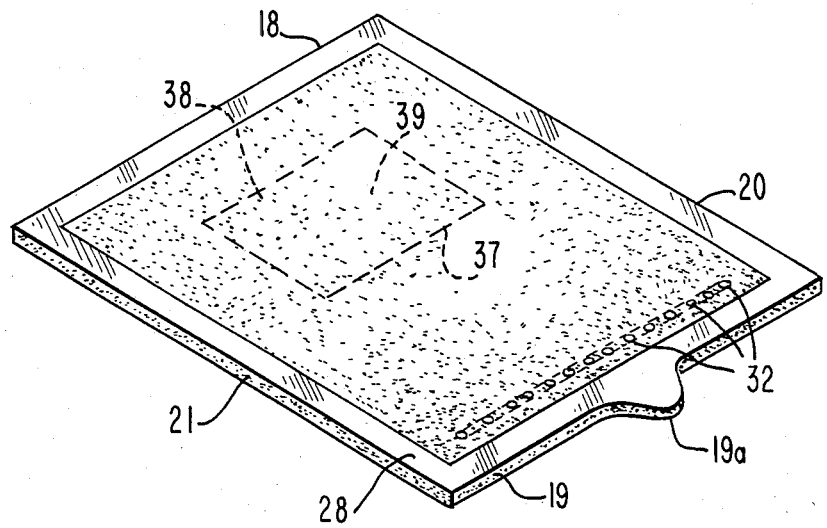
FIG. 7 is a top plan view of the pad showing the pad adapted to be removed from the speculum blade leaving the securing section of the pad shown in FIGS. 5 and 6 on the blade in accordance with the present invention.

Following the dilation and curettage procedure, the pad is removed from the blade and immersed in a saline solution. When the pad is removed, the adhesive section 34 is retained on the speculum blade so as not to interfere with the process of squeezing the pad after it has been immersed in the solution. Detachment of the adhesive section is facilitated through two arrangements. The first is the provision of a perforated border 37 (FIG. 7) on the underside of the pad, the perforated border corresponding to the border of the adhesive section 34. The perforations allow detachment of an outermost section 38 of the pad, the outermost section 38 being attached to the adhesive section 34 and having corresponding dimensions. The bonding strength between the adhesive section 34 and the speculum blade 15 is greater than the strength of the perforated border 37. Similarly, the strength of the perforated border is greater than the bond between the adhesive section 34 and the backing piece 33. These relative strengths are maintained so that the perforated border breaks when moving the pad from the speculum blade and not when the backing is removed.

A second arrangement for facilitating the detachment of the adhesive section 34 is the provision of a second adhesive surface 39 (FIG. 7) of section 34 which attaches adhesive section 34 to the underside of the pad. Again, the strength of the bond between adhesive section 34 and the speculum blade is greater than the strength of the bond between the second adhesive surface 39 and the underside of the pad. Similarly, the bonding strength between the pad and adhesive section is greater than the bond between adhesive section and the backing piece.

Figure 8:
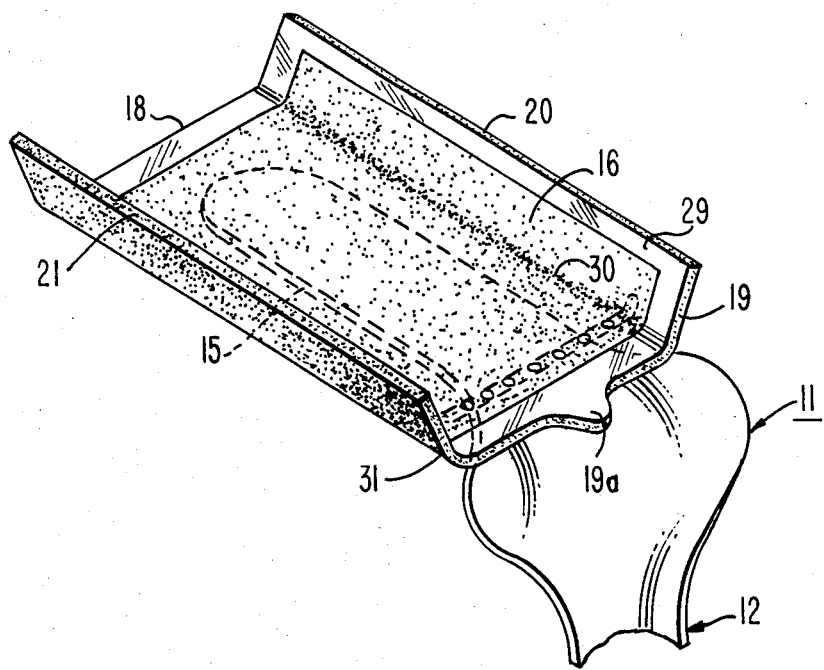
FIG. 8 is a perspective view of the pad shown positioned on a speculum blade.

In the use of the surgical pad as described, the pad is positioned on the speculum blade by sliding the pad on the blade through straps 22 and 23 in one embodiment or placing the pad with adhesive section 34 onto the blade in a second embodiment. With the patient properly anaesthetized and in a dorsal lithotomy position, the side portions of the pad are folded inwardly along fold lines 30 and 31, as shown in FIG. 8 and the speculum blade with the pad positioned thereon in inserted into the vaginal cavity. When in position, and with the cervical canal dilated, the side portions of the pad are permitted to flex outwardly against the side walls of the vaginal cavity, to position the upper surface 16 of the pad adjacent the dilated cervical canal. The physician may then proceed to curette the uterus, directing the curetted tissue onto the adjacent pad. When the curetting has been completed, the side portions of the pad may be folded inwardly so that the speculum blade with the pad positioned thereon may be easily removed from the vaginal cavity. In inserting and withdrawing the speculum blade with the pad thereon and in performing the curettage, the pad is prevented from displacing relative to the speculum blade by virtue of the straps 22 and 23 or adhesive section 34. Consequently, strips and flakes of curetted tissue will not be lost in the upper region of the vaginal cavity necessitating an additional operation in removing such tissue from the vagina.

Figure 9:
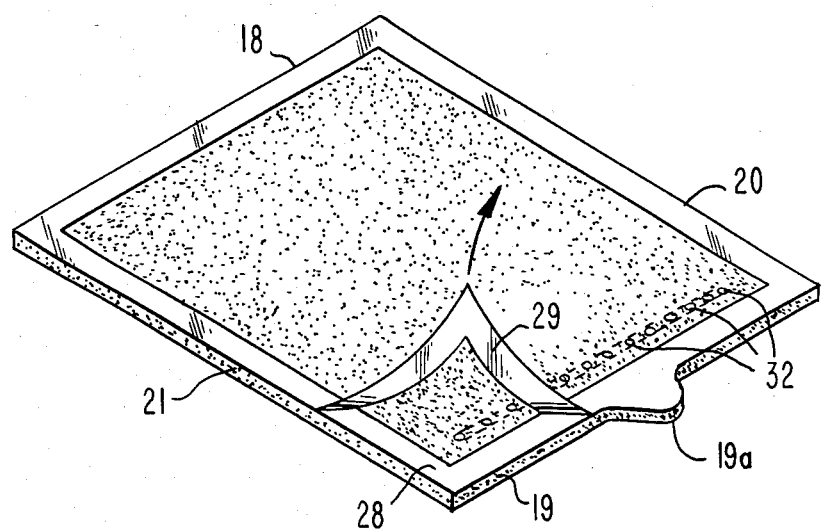
FIG. 9 is a perspective view of the pad, illustrating the manner in which a cover strip may be removed from the pad to expose a peripherally disposed adhesive strip on the upper side of the pad.
Figure 10:
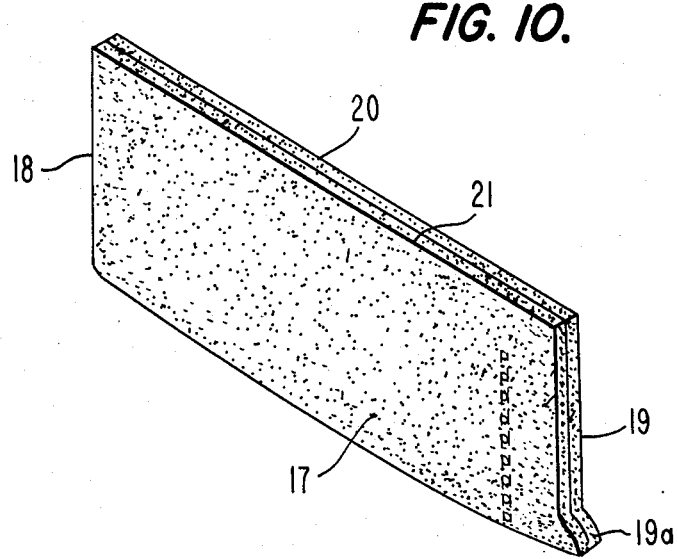
FIG. 10 is a perspective view of the pad shown in FIG. 9, illustrating the pad folded onto itself and adhesively secured together to enclose curetted tissue.

As shown in FIG. 9, the periphery of the upper side 16 of the pad is provided with an adhesive area 28 which is provided with a removable protective or cover strip 29. As shown in FIG. 9, cover strip 29 may be removed to expose the adhesive area 28 and permit the pad to be folded onto itself and adhesively secured together to enclose a specimen of curetted tissue, as shown in FIG. 10.

After the speculum blade and the pad with the collected specimen deposited thereon are removed from the patient, the pad may be removed from the speculum blade and placed on a flat working surface. The cover strip 29 may then be removed, exposing peripheral adhesive strip 28, and the pad may be folded onto itself along a transverse fold line or a longitudinal fold line as shown in FIG. 10 and adhesively secured together to enclose the specimen of curetted tissue. In preparing the specimen for further examination by the pathologist, the folded pad containing the specimen is immersed in a saline solution to dissolve and remove any blood from the specimen. The inflow of the saline solution and the outflow of the solution containing the dissolved blood is accommodated by a number of perforations 32 provided in the pad along rear edge 19 thereof. The folded pad is finally placed in a formalin container for delivery to the pathologist.

Although the pad may be constructed of any clinically suitable material, it is preferred that at least upper surface 16 of the pad be smooth and imperforate to enhance the collection and removal of the specimen. While a pad having a rough or a textured upper surface can be used, the lodging of small particles of specimen in the interstices of the pad will result in the loss of some of the specimen which should be avoided.

The pad may be formed of any suitable material including paper, plastic and fabric. Any fabric may be woven or unwoven, and any woven fabric may be of a loose or close weave. In the use of perforate materials, perforations 32 may be omitted.

It will be appreciated that the use of a conventional pad formed of a solid material or a material having smooth surfaces normally would aggravate the problem of displacement of the pad relative to the speculum blade. The present invention, however, permits the use of such preferable pad materials without incurring any displacement of the pad on the speculum blade either when the blade is being inserted or removed or when the physician is performing the surgical procedure.

Any clinically suitable adhesive and protective adhesive strip may be used with the pad. Although it is preferred that the adhesive strip extend about the periphery of the pad to permit the specimen to be enclosed within the pad when the pad is folded and adhesively secured together, it is contemplated that other arrangements of adhesive areas can be provided.

The adhesive material may be applied directly on the upper surface of the pad or may be disposed on a separate strip applied to the pad. Use of a protective or cover strip for the adhesive areas will depend on the nature of the adhesive material. In addition to conventional adhesive materials including materials having gum bases, it is contemplated that mechanically interlocking means also may be used for securing the pad together to contain the specimen.

From the foregoing detailed description, it will be evident that there are a number of changes, adaptations and modifications of the present invention which come within the province of those persons having ordinary skill in the art to which the aforementioned invention pertains. However, it is intended that all such variations not departing from the spirit of the invention be considered as within the scope thereof as limited solely by the appended claims.

I claim:

1. A surgical pad usable with a speculum blade insertable into the vaginal cavity of a patient in performing dilation and curettage procedures, comprising a pad disposable on said speculum blade for collecting curetted tissue, said pad having an adhesive section on the underside thereof for securing said pad to said speculum blade when said pad is disposed on said blade.

2. A surgical pad according to claim 1 wherein the dimensions of said adhesive section of said pad correspond generally to the dimensions of the upper surface of said speculum blade.

3. A surgical pad according to claim 2 including a removable cover member disposed on said adhesive section.

4. A surgical pad according to claim 3 wherein said removable cover member includes tab means for allowing said cover member to be grasped whereby said cover member can be easily detached from said adhesive section.

5. A surgical pad according to claim 1 wherein said adhesive section is removably attached to the underside of said pad.

6. A surgical pad according to claim 5 wherein said adhesive section is removably attached to an outermost layer of the underside of said pad, said outermost layer having borders which define an area corresponding to the area defined by borders of said adhesive section.

7. A surgical pad according to claim 6 wherein said borders of said outermost layer are perforated to allow said outermost layer to be detached from the underside of said pad.

8. A surgical pad according to claim 7 wherein said perforated borders bind said outermost layer to the underside of said pad and said adhesive section comprises a first adhesive surface which binds said adhesive section to said speculum blade when said pad is disposed thereon.

9. A surgical pad according to claim 8 wherein the binding strength of the perforated borders is less than the strength of the bond between said first adhesive surface and said speculum blade whereby said perforated borders are broken when said pad is removed from said blade.

10. A surgical pad according to claim 8 wherein the binding strength of said perforated borders is greater than the strength of the bond between said first adhesive surface and said removable cover member when said cover member is disposed on said adhesive section whereby said perforated borders are not broken when said cover member is removed from said adhesive section.

11. A surgical pad according to claim 5 wherein said adhesive section includes first and second adhesive surfaces, said first adhesive surface for removably attaching said adhesive section to the underside of said pad and said second adhesive surface for removably attaching said adhesive section to said cover member when said cover member is disposed on said adhesive section and said second adhesive surface for removably attaching said adhesive section to said speculum blade when said pad is disposed on said speculum blade.

12. A surgical pad according to claim 11 wherein the strength of the bond between said adhesive section and the underside of said pad formed by said first adhesive surface is less than the strength of the bond between said adhesive section and said speculum blade formed by said second adhesive surface whereby said adhesive section remains attached to said speculum blade when said pad is removed from said speculum blade.

13. A surgical pad according to claim 10 wherein the strength of the bond between said adhesive section and the underside of said pad formed by said first adhesive surface is greater than the strength of the bond between said adhesive section and said cover member formed by said second adhesive surface whereby said adhesive section remains attached to the underside of said pad when said cover member is removed from said adhesive section.

* * * * *